United States Patent [19]

Barish

[11] Patent Number: 4,827,491

[45] Date of Patent: May 2, 1989

[54] RADIOSURGICAL COLLIMATOR KNIFE

[75] Inventor: Robert J. Barish, New York, N.Y.

[73] Assignee: New York University, New York, N.Y.

[21] Appl. No.: 3,518

[22] Filed: Jan. 15, 1987

Related U.S. Application Data

[63] Continuation-in-part of Ser. No. 924,663, Oct. 30, 1986.

[51] Int. Cl.$^4$ .............................................. A61N 5/10
[52] U.S. Cl. ........................................ 378/65; 378/64;
378/119; 378/147; 378/149
[58] Field of Search .................. 378/12, 34, 64–6, 378/68, 69, 119, 145, 147, 149, 208

[56] References Cited

U.S. PATENT DOCUMENTS

| | | | |
|---|---|---|---|
| 2,139,966 | 12/1983 | Loebell | 378/65 |
| 2,638,554 | 5/1953 | Bartow et al. | 378/147 |
| 3,777,124 | 12/1973 | Pavkovich | 378/65 |
| 4,045,672 | 8/1977 | Waianube | 378/12 |
| 4,157,475 | 6/1979 | Stock et al. | 378/147 |
| 4,250,425 | 2/1981 | Gabbay et al. | 378/12 |
| 4,292,563 | 9/1981 | Gabbay et al. | 378/12 |
| 4,321,473 | 3/1982 | Albert | 378/149 |
| 4,327,293 | 4/1982 | Taumann | 378/147 |
| 4,504,964 | 3/1985 | Cartz et al. | 378/119 |
| 4,608,977 | 9/1986 | Brown | 128/303 B |
| 4,670,894 | 6/1987 | Birnbach et al. | 378/122 |

OTHER PUBLICATIONS

E. O. Backlund et al., "Studies on Grainophryngiomas", Acta Chir Scand, vol. 138, pp. 749–759 (1972).
J. Bradshaw, "Special Report. The Stereotactic Clinical Radiology, Radiosurgery Unit in Sheffield", vol. 37, pp. 277–279 (1986).
F. Columbo, et al., "External Stereotactic Irradiation by Linear Accelerator", Neurosurgery, vol. 16, No. 2, pp. 154–160 (1965).
S. T. Hecht et al., "Stereotactic Heavy-Ion Bragg Peak Radiosurgery for Treatment of Deep Arteriovenous Malformations".
M. D. Heifetz et al., "Single-Beam Radiotherapy Knife", J. Neurosurg., vol. 60, pp. 814–818 (1984).
A. A. Patil et al., "Single Beam Radiosurgery Using the Linear Accelerator and CT Stereotaxic", No. 57.
L. Leksell, "Stereotactic Radiosurgery, Journal of Neurology, Neurosurgery, and Psychiatry", vol. 46, pp. 797–803 (1983).
Leksell Stereotactic Gamma Unit, "Technical Description and Equipment Specifications for Cobalt-60 Gamma Unit for Stereotactic Radiosurgery", (1985).
Philips, "Complete and Integrated Programme for Radiation Therapy" (1982).
F. Pozza et al., "CNS External Stereotaxic Irradiation: A New Role for Radiotherapy", Varian Centerline, pp. 3–4 (1986).
Scanditronix, "Medical Microtrons for Precision Radiotherapy (NM 10, 14 and 22)" (1981).

*Primary Examiner*—Craig E. Church
*Assistant Examiner*—John C. Freeman
*Attorney, Agent, or Firm*—Pennie & Edmonds

[57] ABSTRACT

Apparatus for treatment by radiation of an intracranial portion disposed at a predetermined region, comprises a linear accelerator for supplying a source of energetic electrons, and a collimator disposed adjacent the predetermined region for supplying an X-ray source of radiation to the predetermined region. The collimator includes a plurality of channels oriented toward the predetermined region. Each channel has a target which produces the X-ray radiation when the respective target is selectively exposed to the energetic electrons. The collimator also has a cover layer of radiation attenuation material having a low atomic or Z number and that extends over the outer surface of the collimator but leaves unexposed the plurality of channels. Preferably, the cover layer has a thickness at least equal to the range of the energetic electrons.

A method of treating an intracranial portion with the apparatus of the present invention is also disclosed.

39 Claims, 4 Drawing Sheets

RADIOSURGICAL COLLIMATOR KNIFE

This is a continuation-in-part, of application Ser. No. 924,663, filed Oct. 30, 1986.

TECHNICAL FIELD

The present invention relates to radiation treatment and in particular to radiative treatment of intracranial portions in the human brain.

BACKGROUND ART

The use of radiation for treatment of portions of the human body is well-known in the medical field. Such radiation treatment includes the use of what are typically called linacs or linear accelerators. These devices provide a stream of electrons which may be used directly for therapy or in turn may impact a target material that can thereupon produce X-rays for irradiation of a particular body portion to be treated. In particular the treatment with radiation of intracranial portions of the human brain has been made practical by the use of stereotactic radiosurgery methods as developed by Professor Lars Leksell beginning in 1951.

The gamma knife developed by Professor Leksell is the standard for small-field irradiators. Intended for intracranial or brain irradiation, it consists of a spherical housing containing 201 cobalt sources which are aligned toward a single point in space at the center of the sphere. A set of collimation helmets with precisely drilled holes is provided and one or more of these helmets is used to provide the desired collimation. The precise drilling of the holes in these helmets allows the point of beam convergence to be well controlled.

The gamma knife is not, however, without its drawbacks. Because of these radioactive cobalt sources, the gamma knife includes large shielding structures which greatly increase the cost of construction and operation. As a piece of radiotherapy equipment it is also limited to the small number of patients that have suitable lesions which can be accommodated by the limited region of irradiation. In particular and for this reason, the gamma knife is currently restricted to brain irradiation for treatment of arteriovenous malformations and functional disorders. It has a relatively low dose rate requiring long irradiation times that increase as the cobalt source decays. In time, the array of cobalt sources must be replaced. This process is time-consuming and very costly.

In recent years, attempts have been made to use standard linear accelerators with special collimation systems to accomplish small-volume irradition, for example, in the brain. However, the use of conventional equipment systems for such irradiations suffer from two primary difficulties. First is the problem of achieving the geometric precision required, paticularly if volumes having only 3 or 4 mm cross-sectional diameters are to be irradiated as is often required in intracranial irradiations. This imprecision is due to the lack of structural rigidity inherent in currently available accelerators. Simply put, these machines and the patient support systems sag. In addition, there is the problem of achieving a reasonable or practical does rate when a small collimator aperture is used to provide the relatively small fields of irradiation required in this form of therapy.

I have invented an improved apparatus for treatment with radiation which employs accelerator technology to overcome the aforementioned problems and limitations.

SUMMARY OF THE INVENTION

The present invention is directed to an apparatus for treatment by radiation of a portion of a body disposed at a predetermined region, comprising first means for supplying a first source of radiation; and second means disposed adjacent the predetermined region for supplying a secondary source of radiation to the predetermined region, the second means including at least one channel generally oriented toward the predetermined region and the channel having a radiation target which produces the secondary radiation when the respective target is selectively exposed to the first radiation source, the channel having a first end being closest to the first radiation source and a second end being closest to the predetermined region when the respective target is selectively exposed to the first radiation source. The apparatus further comprises cover means formed of radiation attentuation means and disposed on the second means adjacent the at least one channel so as to attenuate a portion of the first source of radiation to which the respective target is not exposed.

According to one preferred embodiment, the second means includes a plurality of channels generally oriented toward the predetermined region and each channel has a radiation target which produces the secondary radiation when the respective target is selectively exposed to the first radiation source. Each channel has a first end being closest to the first radiation source and a second end being closest to the predetermined region when the respective target is selectively exposed to the first radiation source.

Preferably each radiation target is disposed adjacent the first end of the respective channel. Also the second means is a radiation collimator formed of radiation attentuation material such that the secondary radiation is generally limited in cross-sectional area at said predetermined region to about the cross-sectional area of the second end of the respective channel. Preferably the cover means extends over the second means so as to completely cover the surface of the second means facing the first radiation source means and to leave the radiation targets exposed to the first radiation source. In one preferred embodiment, the channels are oriented so as to generally intersect at a predetermined common focal point. In an alternative embodiment, the second means includes a first plurality of channels and a second plurality of channels. The first plurality of channels is oriented so as to intersect at a first predetermined focal point and the second plurality of channels being oriented so as to intersect at a second predetermined focal point. In yet another alternative embodiment, the channels are oriented so as to provide a radiation cross-section of predetermined configuration and dimension.

According to a preferred embodiment of the present invention, the second end of each of the channels is dimensioned so that the predetermined region is smaller in cross-section than about four millimeters. In addition, each channel is generally uniform in cross-section along its length. Alternatively, the channels can be of different cross-sectional dimensions.

The present invention also is directed to an apparatus for treatment by radiation of an intracranial portion disposed at a predetermined region, comprising means for supplying a source of energetic electrons; and means disposed adjacent the predetermined region for supplying an X-ray source of radiation to the predetermined region, the X-ray means including a plurality of channels generally oriented toward the predetermined region and each channel having a target which produces the X-ray radiation when the respective target is selectively exposed to the energetic electrons, each channel having a first end being closest to the electron source means and a second end being closest to the predetermined region when the respective target is selectively exposed to the energetic electrons. The apparatus further comprises cover means formed of radiation attentuation means and disposed on the second means adjacent the first ends of the plurality of channels so as to attenuate a portion of the first source of radiation to which the radiation targets are not exposed.

According to a preferred embodiment, the cover means extends over the second means so as to completely cover the surface of the second means facing the first radiation source means and to leave the radiation targets exposed to the first radiation source. Also, the cover means is of a uniform thickness. Also, the electron source means is a linear accelerator. The apparatus further comprises means for locating the intracranial portion at the predetermined region. Preferably the locating means is a stereotactic frame. The apparatus further comprises computer means coupled to and controlling the electron source means for supplying a predetermined sequence and duration of selective irradiation of the respective targets. Also provided is a means for supporting and moving the intracranial portion within and about the predetermined region. In one preferred embodiment, a computer means is coupled to and controls the support and movement means for supplying a predetermined sequence and duration of selective irradiation of the respective targets. Also the electron source means comprises a plurality of linear accelerators oriented at a respective plurality of targets for simultaneous irradiation of the targets.

In an alternative embodiment, the present invention relates to an apparatus for treatment by radiation of a portion of a body disposed at a predetermined region, comprising means for supplying a source of energetic electrons and means disposed adjacent the predetermined region for supplying an X-ray source of radiation to the predetermined region, the X-ray means including a channel generally oriented toward the predetermined region and configured so as to approximate the configuration of the body portion to be treated, the channel having a target which produces the X-ray radiation when the target is selectively exposed to the energetic electrons, the channel having a first end being closest to the electron source means and a second end being closest to said predetermined region when the respective target is selectively exposed to the energetic electrons. The apparatus further comprises cover means formed of radiation attentuation means and disposed on the second means adjacent the channel so as to attenuate a portion of the first source of radiation to which the respective target is not exposed.

The present invention is also directed to a method for treating a portion of a body with radiation, comprising positioning the portion of the body to be treated at a predetermined region; supplying a first source of radiation; and disposing a collimator adjacent the predetermined region for supplying a secondary source of radiation to the predetermined region, the collimator including at least one channel generally oriented toward the predetermined region and the channel having a radiation target which produces the secondary radiation when the respective target is selectively exposed to the first radiation source, the channel having a first end being closest to the first radiation source and a second end being closest to the predetermined region when the respective target is selectively exposed to the first radiation source. The collimator further comprises cover means formed of radiation attentuation means and disposed on the second means adjacent the at least one channel so as to attenuate a portion of the first source of radiation to which the respective target is not exposed. Preferably the collimator includes a plurality of channels generally oriented toward the predetermined region and each channel having a radiation target which produces the secondary radiation when the respective target is selectively exposed to the first radiation source.

In a preferred embodiment, the method of treatment with radiation further comprises coupling and controlling the first source of radiation by computer means. The computer means is adapted for supplying a predetermined sequence and duration of selective irradiation of the respective targets.

BRIEF DESCRIPTION OF THE DRAWINGS

The present invention is described in greater detail hereinbelow, with reference to the drawings wherein.

DESCRIPTION OF THE PREFERRED EMBODIMENTS

In the description which follows, any reference to either orientation or direction is intended primarily for the purpose of illustration and is not intended in any way as a limitation of the scope of the present invention.

Figure 1:
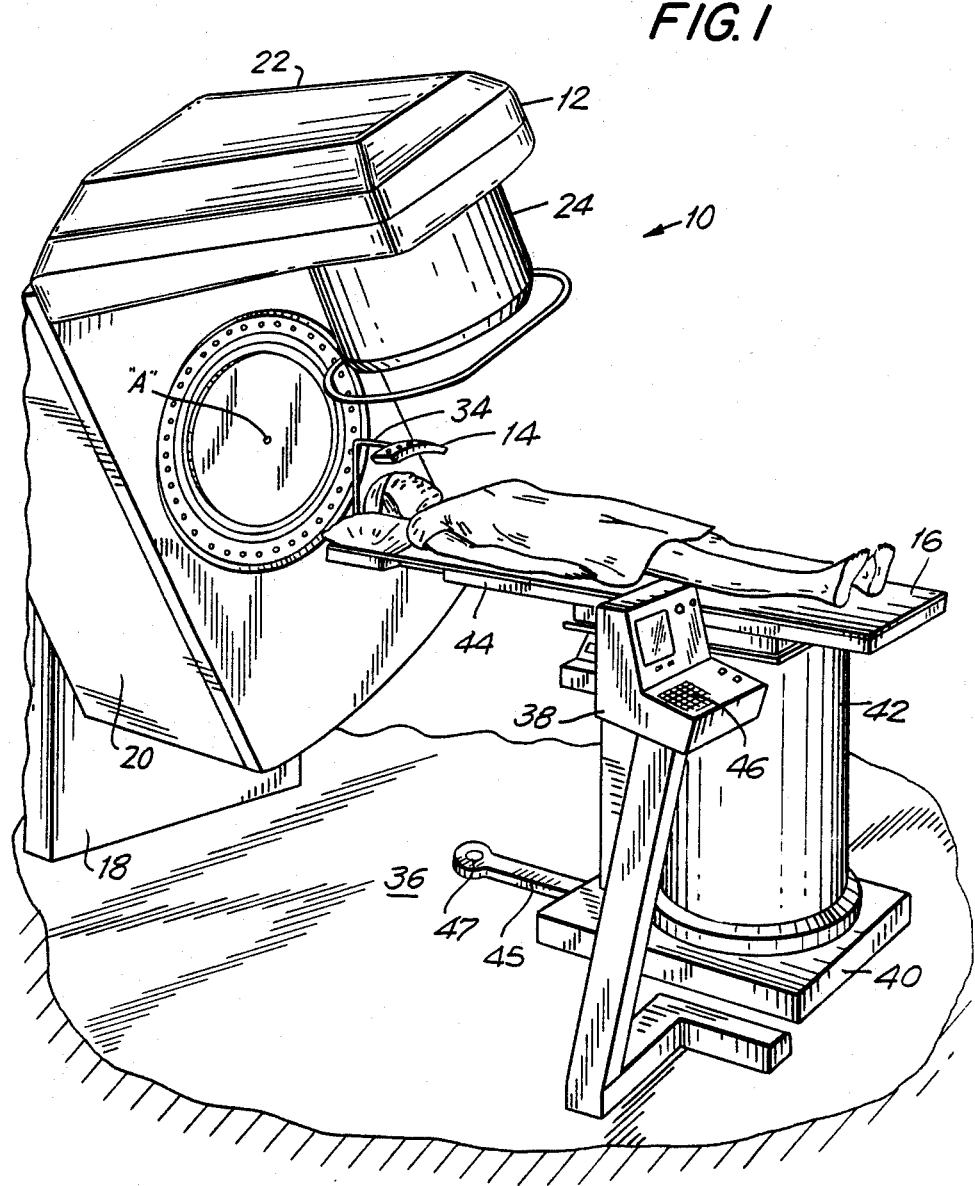
FIG. 1 is a perspective view of a radiosurgical or X-ray knife according to the present invention.

Referring to FIG. 1, a radiosurgical or X-ray knife 10 according to the present invention is illustrated and includes a linear accelerator 12, a collimator 14 and a support table 16. The linear accelerator 12 is of a conventional type such as that shown and described in Philips' brochure entitled "Complete and Integrated Programme for Radiation Therapy" (1982) which is incorporated by reference herein. As noted in the aforementioned brochure, the linear accelerator 12 provides an energetic stream of electrons having a relatively high energy and relatively high intensity at about 4 to 20 MeV (megavolts). The linear accelerator 12 includes a support base 18 which rotatably supports a swivel base 20 that has an outwardly extending arm 22 and a transversely extending collimator 24 as illustrated in FIG. 1. The linear accelerator 12 is thus capable of rotating about its central axis "A" passing through the swivel base 20. Therefore, a stream of highly energetic electrons can be emitted through collimator 24 about the central axis "A".

Figure 2:
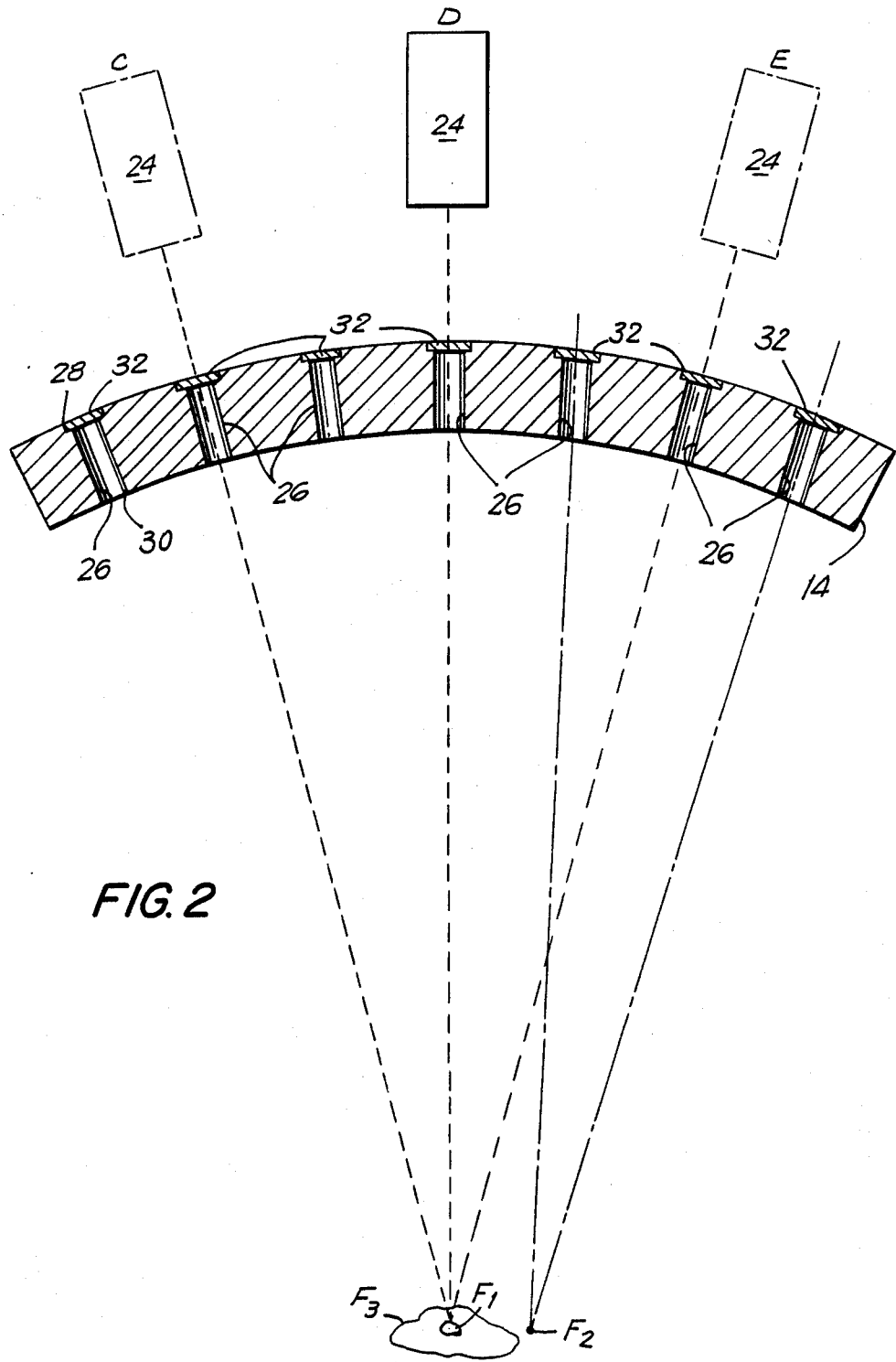
FIG. 2 is a cross-sectional view of the X-ray collimator of the present invention taken along the axis A of FIG. 1.

The collimator 14, as shown more clearly in cross-section in FIG. 2, is formed of a radiation attenuation material and includes a plurality of channels or bores 26 which have a first end 28 closest to the collimator 24 of the linear accelerator 12 and a second end 30 which is closest to focal point F-1. The plurality of channels or bores 26 are oriented so that they have a geometrical convergence at a predetermined region such as at focal point F-1. At the first end 28 of each channel or bore is positioned a target material 32 which can be irradiated by the stream of highly energetic electrons from the linear accelerator 12 and thereupon produce X-ray radiation that travels along the path of the channel or bore 26. As shown more clearly in FIG. 1, the collimator 14 is supported by a frame member 34 which secures the collimator 14 to the support table 16 upon which a patient can rest as shown in FIG. 1. Alternatively, the collimator 14 can be supported from the floor 36 independently of the support table 16.

Accordingly, as the linear accelerator 12 is rotated about its axis "A", a stream of electrons can be directed to strike the different targets 32 in any predetermined or desired sequence and duration so as to provide for a predetermined amount of radiation treatment at the focal point F-1. As shown in FIG. 2, the collimator 24 can be positioned in various steps as shown at "C", "D" and "E" which would indicate sequential or separate positioning of the collimator 24 for purposes of irradiating the respective target materials 32. Alternatively, a series of linear accelerators can be positioned at "C", "D" and "E" as well as additional locations in order to accommodate a plurality of targets 28 simultaneously.

In order to control the operation of the linear accelerator 12, a control panel 38 is coupled by suitable means to the linear accelerator 12 to provide for controlled movement and emission of the energetic stream of electrons. The control panel 38 includes a computer that allows for microprocessor based treatment control. Such control panel is illustrated and described in the aforementioned Philips' brochure. In order that the medical personnel will be protected from radiation during treatment, the control panel 38 or its counterpart can be positioned as well outside of the treatment room. By means of video monitors, the medical personnel can perform their control operations as desired totally outside of the treatment room. Alternatively, the linear accelerator 12 can be manually manipulated between treatment steps.

The control panel 38 is coupled as well to the support table 16 which is also capable of moving the patient within and about the predetermined region of irradiation. As shown in FIG. 1, the support table 16 includes a base 40 on which rests a rotatable pedestal 42 that in turn supports a flat table 44 which is capable of translational movment relative to the base 40. The base 40 is secured to arm 45 which is rotatable about pivot 47. Preferably the pivot 47 is positioned directly below the isocenter of the linear accelerator 12. The isocenter is the intersection point of axis "A" and the central ray of the radiation emitted from collimator 24. Accordingly, there is a multitude of positioning movements which are available as desired to position the targets of collimator 14 relative to and in proper orientation with the electron beam. This allows for variations in the positioning of the channels or bores 26 so as to accommodate any treatment configuration and therefore the channels or bores 26 need not be linearly positioned. As was the case with the linear accelerator 12, all movements of the support table 16 are controllable by the control panel 38. If desired, medical personnel by means of keyboard 46 can manually control each step of the treatment or else program the radiation treatment in advance and employ the automatic computer control capability of panel 38. Alternatively, if desired, the support table can be positioned manually as well without any need for the control panel 38.

As further shown in FIG. 2, a certain plurality of the channels or bores 26 can be oriented so as to converge geometrically upon a second focal point F-2 in order to provide a different point of irradiation with the same collimator 14. Any desired number of focal points can be provided as desired. Alternatively, the channels or bores 26 can be oriented in such a fashion so as to provide an irradiation pattern conforming to the configuration of a predetermined region as indicated by F-3 in FIG. 2. Generally, the second end 30 cross-sectional dimension of the channels or bores 26 is suitability sized so as to provide for an irradiation of a predetermined region at a given focal point. Preferably, the second end 30 has a cross-section of about 4 mm or less. This permits the X-ray knife of the present invention to be suitable for treatment of arteriolvenous malformations or functional disorders in intercranial operations which require such a small region of treatment.

Figure 3:
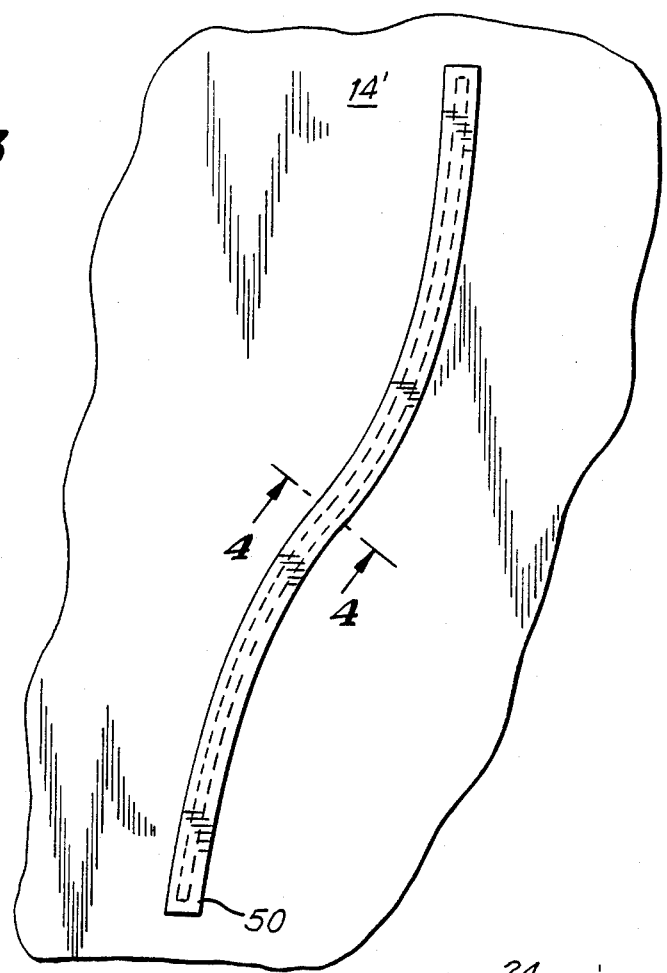
FIG. 3 is a perspective view of an alternative embodiment of an X-ray collimator of the present invention.
Figure 4:
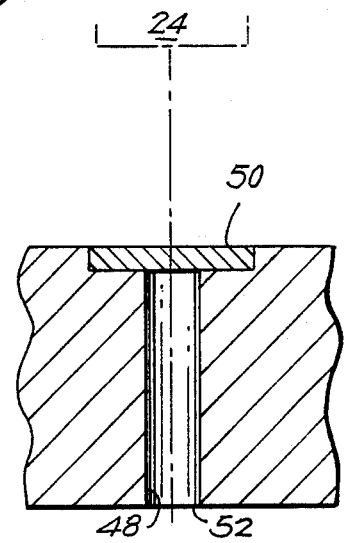
FIG. 4 is a cross-sectional view of the X-ray collimator taken along the lines of 4—4 of FIG. 3.

As shown in FIG. 3, the collimator 14' can be formed of radiation attenuation material in a generally rectangular configuration having a channel 48 which has a continuous target material 50 that approximates in configuration the configuration of a body portion to be treated with radiation. The illustrated configuration in FIG. 3 corresponds to the S shape of the bile duct in the human body. As shown more clearly in FIG. 4, the channel 48 is uniform in cross-section and would provide at its second end 52 a size comparable to the field of irradiation at the predetermined region at which the body portion such as a bile duct is positioned. Accordingly, the collimator 14 can be of any desired size and shape in order to accommodate the configuration of the body portion to be treated with radiation. In the case of intracranial treatments, the collimator 14 can be configured in the shape of a helmet which can be positioned over the patient's head.

Figure 5:
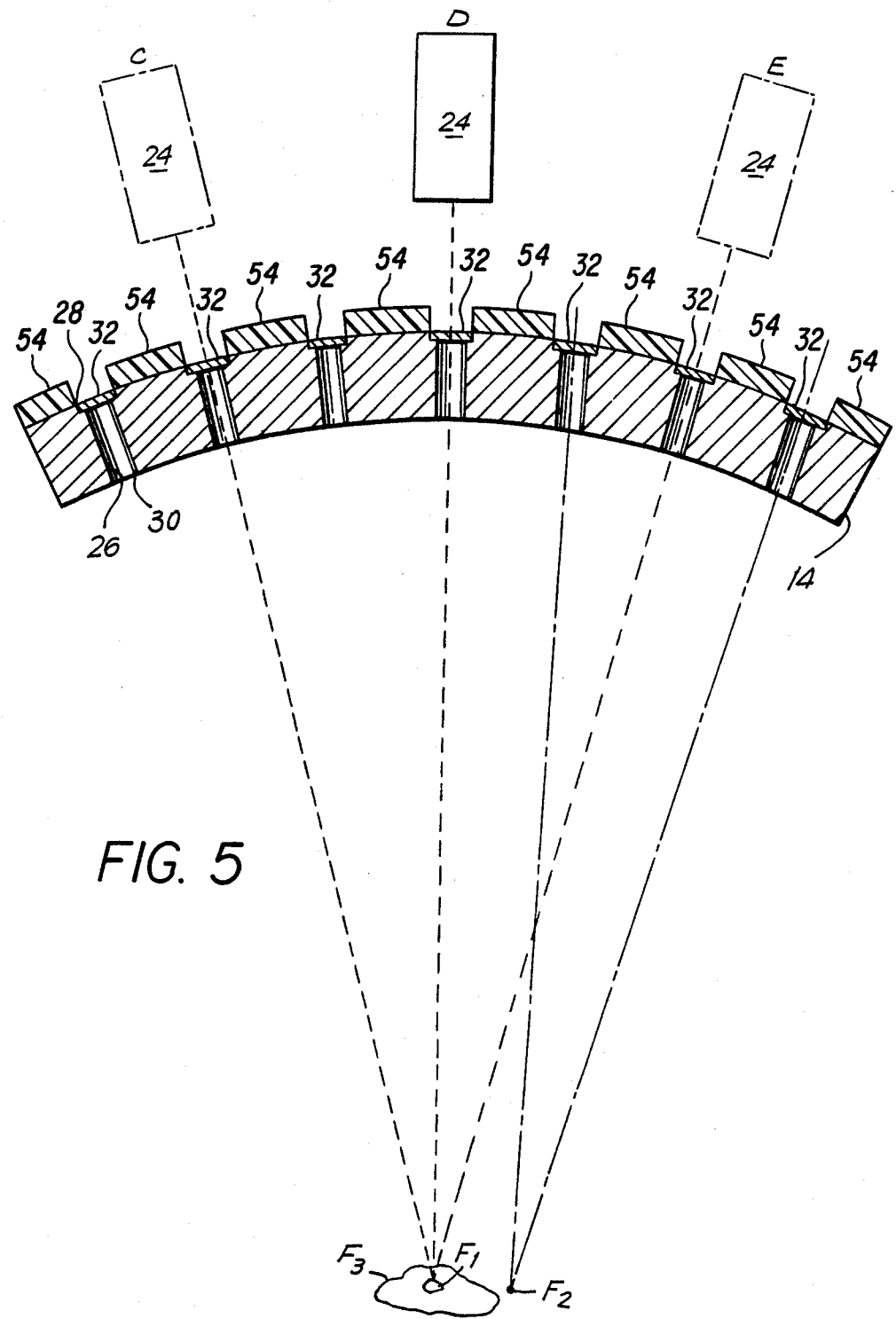
FIG. 5 is a cross-sectional view of yet another alternative embodiment of the X-ray collimator of the present invention.

Referring to FIG. 5, an alternative embodiment to the present invention is disclosed wherein the collimator 14 has positioned on its outer surface facing the linear accelerator 12 a cover layer 54 that extends completely over the outer surface of collimator 14 but leaves exposed the radiation targets 32 which are positioned in the channels or bores 26. As shown in FIG. 5, the cover material 54 includes a plurality of passageways 56 that correspond in dimension with the cross-sectional dimensional area of the respective target 32 over which the passageway 56 is positioned. Preferably the passageways 56 are each of a uniform diameter along their respective lengths. The radiation attentuation material forming cover layer 54 is preferably of a low atomic or Z number. This cover layer 54 serves to absorb electrons from the linear accelerator 12 and thereby prevent any secondary radiation from being produced at locations other than the targets 32. Although preferably the cover layer 54 is of a uniform thickness, it can also be of varying thicknes. It is preferred that the thickness be at least equal to the range of the energetic electrons from the linear accelerator 12 to prevent unwanted secondary radiation.

According to the X-ray knife of the present invention, the geometric uncertainty of commercially available linear accelerators is avoided while providing for a practical or reasonable dose of radiation in the treatment process. A typical minimum practical dosage rate is 1 gray/minute, i.e., 100 rads/minute, which is comparable to that obtained with the gamma knife. However, by using a high electron beam current, a dose rate of 10-100 times the aforementioned practical dose rate can be achieved with the device of the present invention. Accordingly, the radiosurgical knife allows for reduced treatment times not otherwise presently available. Therefore, the linear accelerator of the subject radiosurgical knife becomes more quickly available for other conventional uses.

The positioning of the body portion to be treated can be performed by any of the localization methods known in the medical field and the present invention is not limited by the localization method employed. One preferred method of positioning the body portion such as intracranial portions in the brain at the predetermined region for treatment by radiation includes the stereotactic frame. Such method is well-known and is described in J. D. Bradshaw, "The Stereotactic Radiosurgery Unit in Sheffield", *Clinical Radiology*, vol. 37, pages 277-79 (1986) and Lars Leksell, "Stereotactic Radiosurgery", *Journal of Neurology, Neurosurgery, and Psychiatry*, vol. 46, pages 797-803 (1983) which are incorporated herein in their entirety. The collimator 14 can alternatively be supported or affixed to the stereotactic frame which is illustrated and described in the aforementioned publications.

The present invention has been described in detail with particular emphasis on the preferred embodiments thereof. However, it should be understood that variations and modifications within the spirit and scope of the invention may occur to those skilled in the art to which the invention pertains.

I claim:

1. Apparatus for therapeutic treatment by radiation of a portion of a body disposed at a predetermined region, comprising:
   1. first means for supplying a first source of high energy particle radiation;
   2. second means disposed adjacent the predetermined region for supplying a secondary source of radiation to the predetermined region, wherein said secondary source produces radiation at an energy level appropriate for therapeutic treatment by radiation, said second means including at least one bore generally oriented toward the predetermined region and said bore having respective radiation target which produces the secondary radiation when said respective target is selectively exposed to said first source of high energy particle radiation, said bore having a first end being closest to said first source of high energy particle radiation and a second end being closest to said predetermined region when said respective target is selectively exposed to said first source of high energy particle radiation; and
   3. cover means formed of radiation attenuation means and disposed on said second means adjacent said at least one bore so as to attenuate a portion of said first source of high energy particle radiation to which said respective target is not exposed.

2. Apparatus for therapeutic treatment by radiation of a portion of a body disposed at a predetermined region, comprising:
   1. first means for supplying a first source of high energy particle radiation;
   2. second means disposed adjacent the predetermined region for supplying a secondary source of radiation to the predetermined region, wherein said secondary source produces radiation at an energy level appropriate for therapeutic treatment by radiation, said second means including a plurality of bores generally oriented toward the predetermined region and each bore having a respective radiation target which produces the secondary radiation when said respective target is selectively exposed to said first source of high energy particle radiation, each said bore having a first end being closest to said first source of high energy particle radiation and a second end being closest to said predetermined region when said respective target is selectively exposed to said first source of high energy particle radiation; and
   3. cover means formed of radiation attenuation means and disposed on said second means adjacent said first ends of said plurality of bores so as to attenuate a portion of said first source of high energy particle radiation to which said radiation targets are not exposed.

3. The apparatus according to claim 2 wherein each said respective radiation target is disposed adjacent said first end of each said bore.

4. Apparatus for treatment by radiation of a portion of a body disposed at a predetermined region, comprising:
   a. first means for supplying a first source of high energy particle radiation;
   b. second means disposed adjacent the predetermined region for supplying a secondary source of radiation to the predetermined region, said second means including a plurality of bores generally oriented toward the predetermined region and each bore having a respective radiation target which produces the secondary radiation when said respective target is selectively exposed to said first source of high energy particle radiation, each said bore having a first end being closest to said first source of high energy particle radiation and a second end being closest to said predetermined region when said respective target is selectively exposed to said first source of high energy particle radiation; and
   c. cover means formed of radiation attenuation means and disposed on said second means adjacent said first ends of said plurality of bores so as to attenuate a portion of said first source of high energy particle radiation to which said radiation targets are not exposed;

wherein each said radiation target is disposed adjacent said first end of said respective bore and wherein said second means is a radiation collimator formed of radiation attenuation material such that said secondary radiation is generally limited in cross-sectional area at said predetermined region to about the cross-sectional area of said second end of said respective bore.

5. The apparatus according to claim 4 wherein said cover means extends over said second means so as to completely cover the surface of said second means facing said first radiation source means and to leave said respective radiation targets exposed to said first radiation source.

6. The apparatus according to claim 5 wherein said bores are oriented so as to generally intersect at a predetermined common focal point.

7. The apparatus according to claim 5 wherein said second means includes a first plurality of bores and a second plurality of bores, said first plurality of bores being oriented so as to intersect at a first predetermined focal point and said second plurality of bores being oriented so as to intersect at a second predetermined focal point.

8. The apparatus according to claim 5 wherein said bores are oriented so as to provide a radiation cross-section of predetermined configuration and dimension.

9. The apparatus according to claim 5 wherein said second end of each of said bores is dimensioned so that said predetermined region is smaller in cross-section than about four millimeters.

10. The apparatus according to claim 5 wherein each said bore is generally uniform in cross-section along its length.

11. The apparatus according to claim 5 wherein said bores are of different cross-sectional dimensions.

12. Apparatus for therapeutic treatment by radiation of an intracranial portion disposed at a predetermined region, comprising:
  1. first means for supplying a source of energetic electrons;
  2. second means disposed adjacent the predetermined region for supplying an X-ray source of radiation to the predetermined region, wherein said secondary source produces radiation at an energy level appropriate for therapeutic treatment by radiation, said second means including a plurality of bores generally oriented toward the predetermined region and each bore having a respective target which produces the X-ray radiation when said respective target is selectively exposed to said energetic electrons, each said bore having a first end being closest to said first means and a second end being closest to said predetermined region when said respective target is selectively exposed to said energetic electrons; and
  3. cover means formed of radiation attenuation means and disposed on said second means adjacent said first ends of said plurality of bores so as to attenuate a portion of said source of energetic electrons to which said radiation targets are not exposed.

13. The apparatus according to claim 12 wherein each said respective target is disposed adjacent said first end of each said respective bore.

14. The apparatus according to claim 13 wherein said second means includes a collimator formed of radiation attenuation material such that said X-ray radiation is generally limited in cross-sectional area at said predetermined region to about the cross-sectional area of said second end of each said respective bore.

15. The apparatus according to claim 14 wherein said cover means extends over said second means so as to completely cover the surface of said second means facing said first means and to leave said respective radiation targets exposed to said first means.

16. The apparatus according to claim 15 wherein said cover means is formed of radiation attenuation means having a low atomic number so as to absorb electrons from said first means and so as to generally prevent X-ray radiation from being produced at locations other than said respective target.

17. The apparatus according to claim 16 wherein said cover means is of a thickness at least equal to the range of the energetic electrons.

18. The apparatus according to claim 17 wherein said cover means is of a uniform thickness.

19. The apparatus according to claim 15 wherein said first means is a linear accelerator.

20. The apparatus according to claim 15 wherein said bores are oriented so as to generally intersect at a predetermined common focal point.

21. The apparatus according to claim 15 wherein said second means includes a first plurality of bores and a second plurality of bores, said first plurality of bores being oriented so as to intersect at a first predetermined focal points and said second plurality of bores being oriented so as to intersect at a second predetermined focal point.

22. The apparatus according to claim 15 wherein said bores are oriented so as to provide a radiation cross-section of predetermined configuration and dimension.

23. The apparatus according to claim 15 wherein said second end of each of said bores is dimensioned so that said predetermined region is smaller in cross-section than about four millimeters.

24. The apparatus according to claim 15 wherein each said bore is generally uniform in cross-section along its length.

25. The apparatus according to claim 15 wherein said bores are of different cross-sectional dimensions.

26. The apparatus according to claim 15 further comprising means for locating the intracranial portion at the predetermined region.

27. The apparatus according to claim 26 wherein said locating means is a stereotactic frame.

28. The apparatus according to claim 15 further comprising computer means coupled to and controlling said first means for supplying a predetermined sequence and duration of selective irradiation of said respective targets.

29. The apparatus according to claim 15 further comprising means for supporting and moving the intracranial portion within and about the predetermined region.

30. The apparatus according to claim 29 further comprising computer means coupled to and controlling said support and movement means for supplying a predetermined sequence and duration of selective irradiation of said respective targets.

31. The apparatus according to claim 30 wherein said first means comprises a plurality of linear accelerators oriented at a plurality of said respective targets for simultaneous irradiation of said respective targets.

32. The apparatus according to claim 15 wherein said first means comprises a plurality of linear accelerators oriented at a respective plurality of targets for simultaneous irradiation of said targets.

33. Apparatus for therapeutic treatment by radiation of a portion of a body disposed at a predetermined region, comprising:
  1. means for supplying a source of energetic electrons;
  2. means disposed adjacent the predetermined region for supplying an X-ray source of radiation to the predetermined region, wherein said secondary source produces radiation at an energy level appropriate for therapeutic treatment by radiation, said X-ray means including a bore generally oriented toward the predetermined region and configured so as to approximate the configuration of the body portion to be treated, said bore having a target which produces the X-ray radiation when said target is selectively exposed to said energetic electrons, said channel having a first end being closest to said electron source means and a second end being closest to said predetermined region when said target is selectively exposed to said energetic electrons; and 3. cover means formed of radiation attenuation means having a relatively low atomic number and disposed on said second means adjacent said bore so as to attenuate a portion of said first source of radiation to which said target is not exposed, said cover means having a thickness at least equal the range of the energetic electrons.

34. A method for treating a portion of a body with radiation, comprising:
1. positioning the portion of the body to be treated at a predetermined region;
2. supplying a first source of high energy particle radiation; and
3. disposing a collimator adjacent the predetermined region for supplying a secondary source of radiation to the predetermined region, said collimator including at least one bore generally oriented toward the predetermined region and said bore having a respective radiation target which produces the secondary radiation when said respective target is selectively exposed to said first source of high energy particle radiation, said channel having a first end being closest to said first source of high energy particle radiation and a second end being closest to said predetermined region when said first source of high energy particle radiation; said collimator further including cover means formed of radiation attenuation means and disposed on said collimator adjacent said at least one channel so as to attenuate a portion of said first source of high energy particle radiation to which said respective target is not exposed.

35. A method for treating a portion of a body with radiation, comprising:
1. positioning the portion of the body to be treated at a predetermined region;
2. supplying a first source of high energy particle radiation; and
3. disposing a collimator disposed adjacent the predetermined region for supplying a secondary source of radiation to the predetermined region, said collimator including a plurality of bores generally oriented toward the predetermined region and each bore having a respective radiation target which produces the secondary radiation when said respective target is selectively exposed to said first source of high energy particle radiation, each said bore having a first end being closest to said first source of high energy particle radiation and a second end being closest to said predetermined region when said respective target is selectively exposed to said first source of high energy particle radiation, said collimator further including cover means formed of radiation attenuation means and disposed on said collimator adjacent said first ends of said plurality of channels so as to attenuate a portion of said first source of high energy particle radiation to which said radiation targets are not exposed.

36. The method according to claim 35 wherein said first source of high energy particle radiation is a source of energetic electrons.

37. The method according to claim 36 wherein said secondary source of radiation is X-ray radiation.

38. The method according to claim 35 wherein said positioning of the body portion is performed with a stereotactic frame.

39. The method according to claim 35 further comprising coupling and controlling said first source of high energy particle source of radiation by computer means, said computer means supplying a predetermined sequence and duration of selective irradiation of said respective targets.

* * * * *